United States Patent
Marcelloni et al.

(10) Patent No.: US 11,987,404 B2
(45) Date of Patent: *May 21, 2024

(54) METHOD FOR FILLING CONTAINERS WITH A POWDER

(71) Applicant: NTC S.R.L., Milan (IT)

(72) Inventors: Luciano Marcelloni, Milan (IT); Federico Bertocchi, Milan (IT)

(73) Assignee: NTC S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/279,549

(22) PCT Filed: Feb. 26, 2020

(86) PCT No.: PCT/IB2020/051650
§ 371 (c)(1),
(2) Date: Mar. 24, 2021

(87) PCT Pub. No.: WO2020/174423
PCT Pub. Date: Sep. 3, 2020

(65) Prior Publication Data
US 2021/0316889 A1  Oct. 14, 2021

(30) Foreign Application Priority Data
Feb. 27, 2019 (IT) ................. 102019000002857

(51) Int. Cl.
| | |
|---|---|
| *B65B 1/14* | (2006.01) |
| *A23L 27/30* | (2016.01) |
| *A23P 10/40* | (2016.01) |
| *A61J 1/00* | (2023.01) |
| *A61K 9/14* | (2006.01) |
| *A61K 31/047* | (2006.01) |
| *B65B 1/08* | (2006.01) |

(52) U.S. Cl.
CPC .............. *B65B 1/14* (2013.01); *A23L 27/34* (2016.08); *A23P 10/40* (2016.08); *A61J 1/00* (2013.01); *A61K 9/14* (2013.01); *A61K 31/047* (2013.01); *B65B 1/08* (2013.01); *A23V 2002/00* (2013.01); *B65B 2230/02* (2013.01)

(58) Field of Classification Search
CPC ......... B65B 1/14; B65B 1/08; B65B 2230/02; A23L 27/34; A23P 10/40; A61J 1/00; A61K 9/14; A61K 31/047; A23V 2002/00
See application file for complete search history.

(56) References Cited

U.S. PATENT DOCUMENTS

| | | |
|---|---|---|
| 2003/0003229 A1 | 1/2003 | Walton |
| 2003/0114430 A1 | 6/2003 | MacLeod et al. |
| 2012/0156496 A1* | 6/2012 | Boit ............ A61K 9/2018 |
| | | 428/402 |

FOREIGN PATENT DOCUMENTS

| | | |
|---|---|---|
| CN | 1884243 A | 12/2006 |
| CN | 100413834 C | 8/2008 |
| CN | 102482184 * | 5/2012 |
| EA | 000968 B1 | 8/2000 |
| EP | 1241112 A2 | 9/2002 |
| EP | 3015102 A1 | 5/2016 |
| NO | 327452 B1 | 7/2009 |
| UZ | 2913 C | 12/2005 |
| WO | WO 2010/141751 A1 | 12/2010 |
| WO | WO 2013/187088 A1 | 12/2013 |
| WO | WO 2020/174425 A1 | 9/2020 |

OTHER PUBLICATIONS

H.A. Leniger and W.A. Beverloo, Food Process Engineering (D. Reidel Publishing Co.) 247-48 (1975) ("Leniger").*
Paulo et al., "Safety of Mannitol Use in Bowel Preparation: a prospective assessment of intestinal methane (CH4) levels during colonoscopy after mannitol and sodium phosphate (NaP) bowel cleansing", Arquivos De Gastroenterologia, 2016, 53(3): 196-202.
Rowe et al., "Mannitol" in "Handbook of Pharmaceutical Excipients, 7th Edition", Pharmaceutical Press, 2012, pp. 479-482.
Anonymous: "Mannitol poeder (100 gram)" PoederWinkel.nl, Jan. 2018, 8 pages (English + Original).
Malori, "Oral drug reconstitution: Making it easy and accurate via packaging innovation" On Drug Delivery, vol. 88, Jul. 2018, pp. 18-21.
Rowe et al., "Handbook of pharmaceutical excipients, Mannitol" Pharmaceutical Press, Jan. 2006, pp. 449-453.
Saheball et al., "A randomized controlled trial comparing polyethylene glycol + ascorbic acid with sodium picosulphate + magnesium citrate solution for bowel cleansing prior to colonoscopy" Irish Journal of Medical Science, vol. 184, No. 4, Aug. 2014, pp. 819-823.

* cited by examiner

*Primary Examiner* — Shirley V Gembeh
(74) *Attorney, Agent, or Firm* — James S. Keddie; Bozicevic, Field & Francis LLP

(57) ABSTRACT

The present invention regards a method for filling containers with a single-dose composition comprising or, alternatively, consisting of mannitol in powder form. Such process comprises the following steps: a) breaking up a coherent mass of powder mannitol, so as to obtain a broken-up mass from said coherent mass; c) filling a plurality of containers with the broken-up mass of step a), wherein a bulk density of the coherent mass is smaller than a bulk density of the broken-up mass.

16 Claims, 6 Drawing Sheets

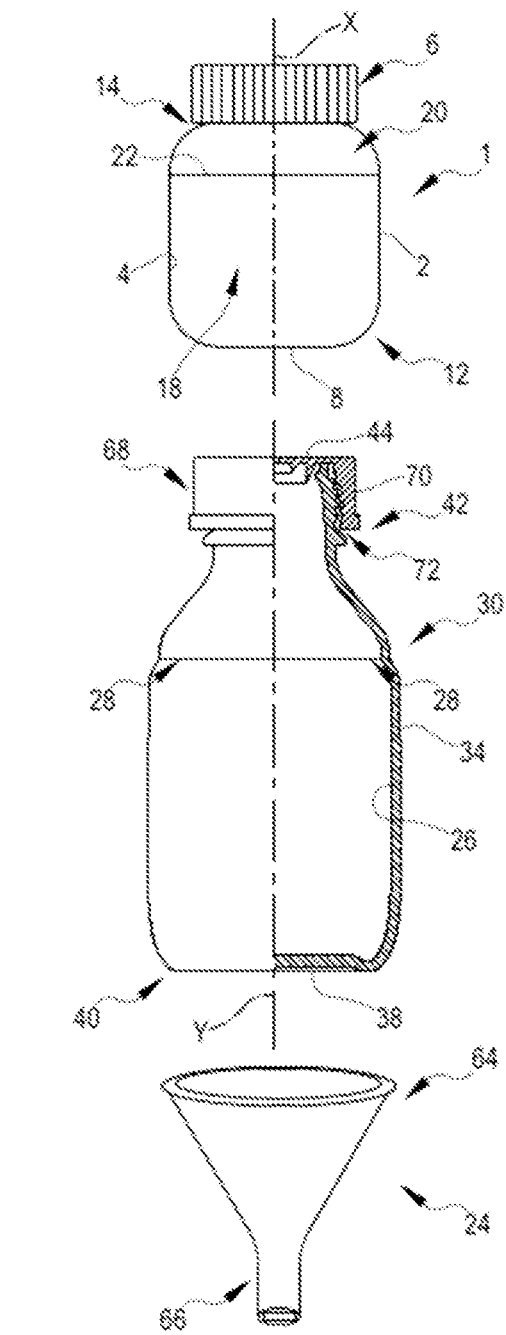

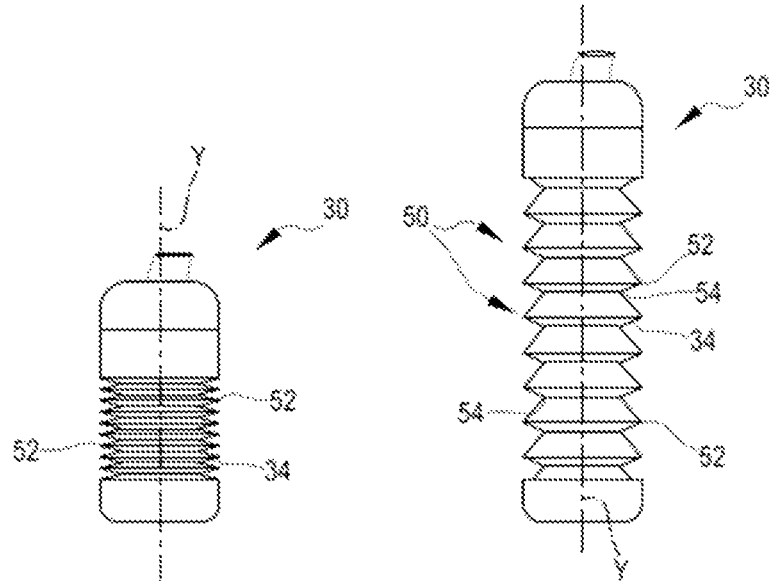
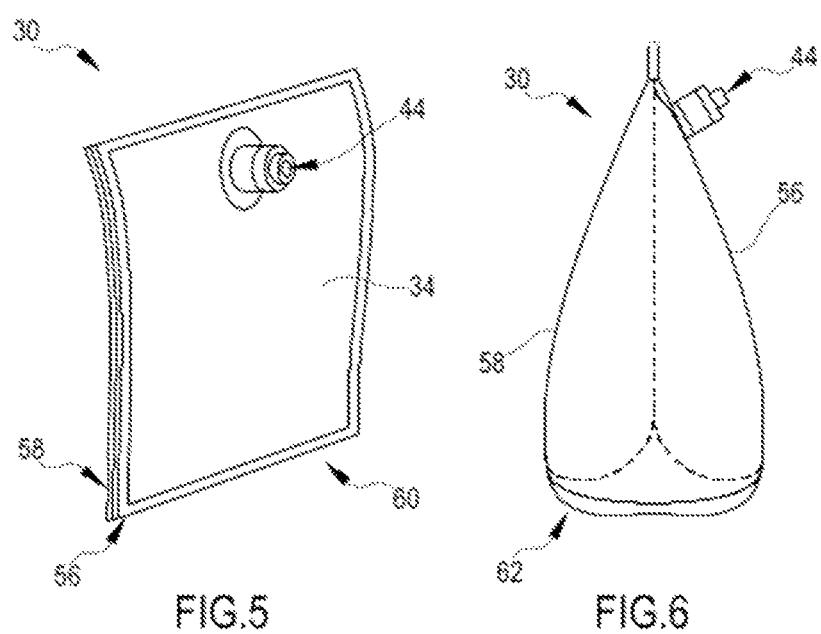

METHOD FOR FILLING CONTAINERS WITH A POWDER

CROSS-REFERENCE TO RELATED APPLICATIONS

This application is a § 371 national phase of International Application No. PCT/IB2020/051650, filed on Feb. 26, 2020, which claims the benefit of Italian Application No. 102019000002857, filed on Feb. 27, 2019, all of which applications are incorporated by reference herein.

The present invention regards a method for filling containers with a composition.

Mannitol (CAS N° 69-65-8; otherwise referred to as "D-mannitol" or "mannite") is a chiral alditol, with six hydroxyl groups on an aliphatic chain consisting of six saturated carbon atoms.

At ambient temperature, mannitol appears as white solid, odourless and non-hygroscopic. Mannitol is used as a sweetener in foods for diabetic people due to the fact that it is poorly absorbed by the bowel.

Over the years, mannitol has been widely used in the pharmaceutical industry and in the gastroenterological industry, due to its osmotic diuretic characteristics and in that it is an ancient remedy for constipation. The sweet taste of mannite makes its use is particularly appreciated by children.

Mannose, an oxidation product of mannitol, has also proven to be particularly suitable for use in pediatrics, since it acts as a prebiotic for bacterial strains of the gut flora.

A use of mannitol that has been investigated in the past is its use in emptying the colon prior to endoscopic examinations, carried out by ingesting high doses of mannitol pre-dissolved in water. In particular, the action of emptying the colon occurs in 4 or 5 hours after ingesting mannitol pre-dissolved in water. The use of mannitol pre-dissolved in water has several advantages over other substances having the function of emptying the colon (for example Macrogol®, based on polyethylene glycol). As a matter of fact, Macrogol®, having a slower induction, requires at least one first intake the day before, and a second intake on the day of the examination. Furthermore, the taste of some of such known substances is markedly worse, being very bitter, with respect to the taste of mannitol.

Nevertheless, the use of mannitol solutions reveals some limitations and drawbacks. As a matter of fact, in the past there have been cases of bowel explosion of patients who had been subjected to gastric emptying by ingesting mannitol pre-dissolved in water. These explosions have been attributed to incomplete cleaning of the colon, with permanence—in the bowel—of methane-producing bacteria, or hydrogen-reducing producers (see for example the technical problem of the prior art document EP3015102A1, paragraphs [0002]-[0012]). Specifically, following some cases, it was observed that a portion of mannitol that remained undissolved in the solution taken by the patient had reduced the ingested dose that would have been required for proper bowel cleansing and, as discussed above, only a partial dissolution of mannitol in solution can be a contributing cause of explosion.

According to a further aspect, in cases where the user of the preparation is an elderly person, this could limit the shaking required for the full dissolution of mannitol in solution due to various factors, by way of example, due to pain in the joints, distraction, lack of patience, or the like.

Moreover, an incomplete intake of mannitol in solution, and therefore an incomplete cleansing of the bowel could also limit correct diagnosis, which may not be useful in a statistically larger number of patients.

It is therefore extremely important that, for this specific use, mannitol be completely dissolved in solution, so that it can be administered effectively, completely and reproducibly.

It should also be pointed out that, although a reduction in the grain size of the mannitol powder has favourable effects on the dissolution rate of such substance, such reduction has the drawback of markedly jeopardising the flowability of the powder, and therefore make management thereof on an industrial scale more complex. These circumstances have thus posed the present inventors a new technological-productive challenge.

The present invention therefore lies in the previous context, setting out to provide a method capable of obviating the difficult handling and the complex packing of powder mannitol in the primary storage container thereof, before use.

As a matter of fact, the manufacture, handling and packing of the present powder composition in the container (which constitutes the primary container), in an extremely fine grain size state, represents a major technological challenge.

These objectives are achieved through a process for filling containers according to claim 1. The claims dependent on this one show preferred embodiments of the present invention.

The present invention will now be described based on the attached drawings, provided solely by way of non-limiting example, wherein:

FIG. 2 shows a schematic view of a kit subject of the present invention, according to a possible embodiment, wherein the container is shaped differently with respect to FIG. 1;

FIGS. 3, 4 show a dissolving container according to a first embodiment, respectively in an at least partially collapsed configuration and in an expanded configuration;

FIGS. 5, 6 show a dissolving container according to a second embodiment, respectively in an at least partially (for example: completely) collapsed configuration and in an expanded configuration;

Figure 9:
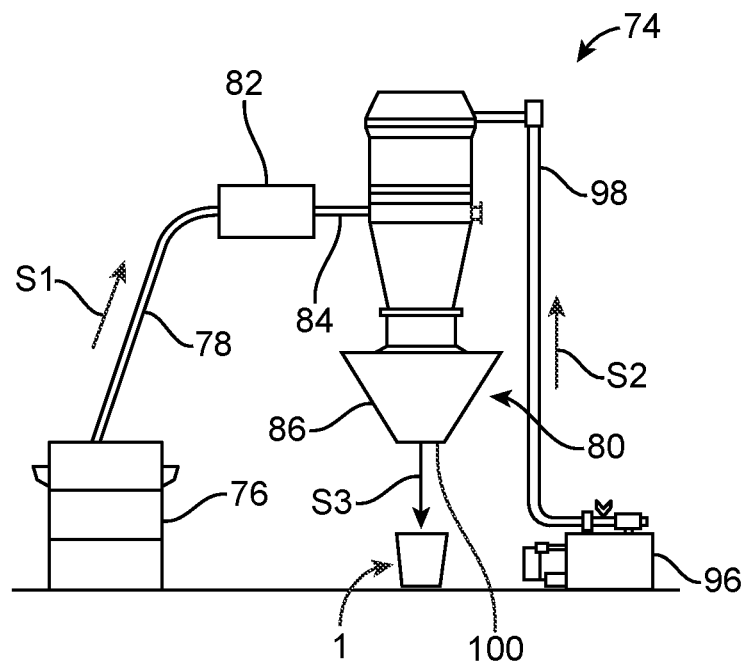
Figure 10:
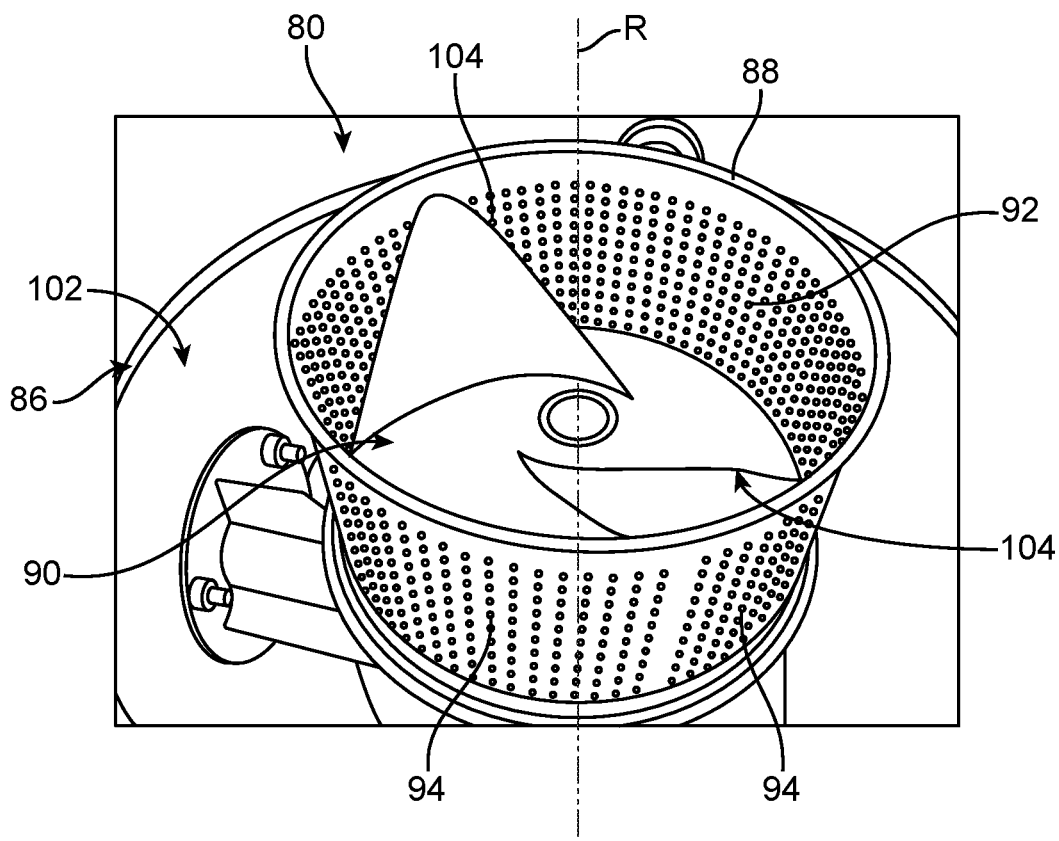

FIG. 9 schematically exemplifies an equipment that can be used in the present filling method;

FIG. 10 is a perspective view of a drum sieve shaker that can be used in the equipment according to FIG. 9.

Figure 11:
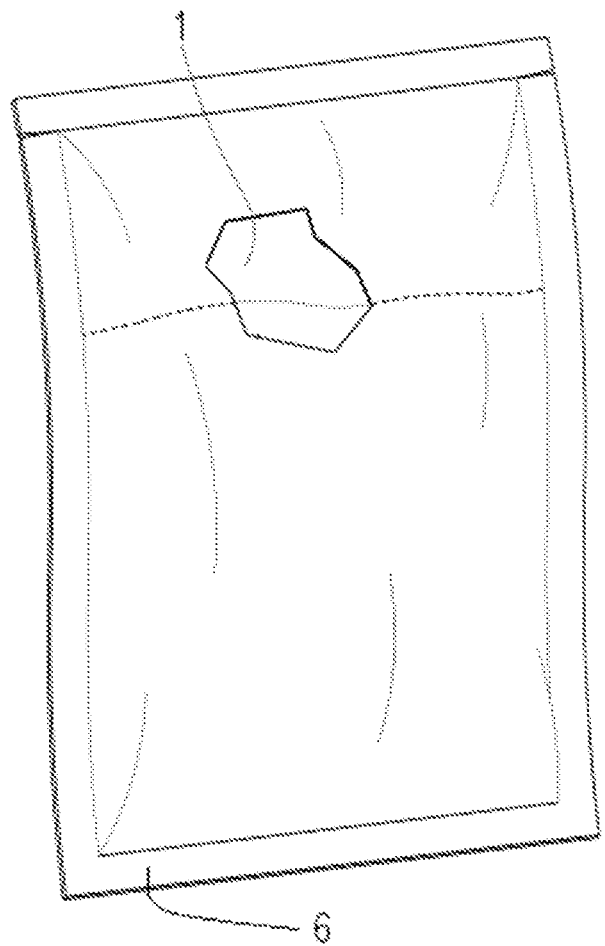

FIG. 11 illustrates a plan view of a heat-sealed envelope 1 object of the present invention, according to a possible embodiment.

It should be observed that the dimensional ratios shown in the previous figures do not represent limitations to the present invention.

The aforementioned objectives were achieved through a process for filling containers (preferably single-dose containers) with a composition (preferably a single-dose composition) comprising or, alternatively, consisting of mannitol in powder form.

Such process comprises the following steps:
a) breaking up a coherent mass of mannitol powder, so as to obtain a broken-up mass from such coherent mass;

b) preferably mixing the broken-up mass of step a);
c) filling a plurality of containers (preferably single-dose containers) with the broken-up mass of step a) or step b), wherein a bulk density of the coherent mass is smaller than a bulk density of the broken-up mass.

It should be observed that the bulk density values mentioned in this description are to be understood as being measured at ambient temperature and pressure.

As far as the terminology used in this description is concerned, the expression "coherent mass" is used to indicate a mass consisting of powder particles closely adjacent and joined to each other, cohesive, and forming a plurality of lumps or agglomerates.

By contrast, the expression "broken-up mass" is used to indicate a mass of mannitol powder which, with respect to the coherent mass, has a smaller amount or concentration of lumps or agglomerates. More precisely, the broken-up mass could be substantially devoid of lumps or agglomerates.

According to an embodiment, step i) could comprise a step for separating and/or crushing the coherent mass or, more precisely, the powder particles it consists of.

According to an embodiment, in step c) each container is filled with a metered amount of mannitol powder comprised from 50 to 200 grams.

According to another embodiment, the bulk density of the coherent mass is smaller than a bulk density of the broken-up mass by a percentage comprised from 1% to 40%, preferably comprised from 1% to 30%, even more preferably comprised from 5% to 15%, with respect to the bulk density of the broken-up mass. According to an embodiment, step a) comprises a breaking-up with a centrifugal force, preferably exerted by means of a drum centrifugal sieve shaker.

According to a further embodiment, step a) comprises the following sub-steps:
a.i) sieving the coherent mass of mannitol powder; and
a.ii) packing the product of sub-step a.i), preferably in a uniform and/or reproducible manner.

According to an embodiment, sub-steps a.i) and a.ii) are at least partially contextual.

According to a further embodiment, in sub-step a.ii)—the powder mannitol is forced through a mesh with a clear span comprised from 2.0 to 5.0 millimetres, preferably comprised from 2.0 and 4.0 millimetres, more preferably comprised from 2.5 to 3.5 millimetres, even more preferably of 3.0 millimetres.

According to a yet further embodiment, the bulk density of mannitol powder at the end of sub-step a.ii) is comprised from 0.66 to 0.90 g/ml, preferably comprised from 0.66 to 0.84 g/ml, more preferably comprised from 0.68 to 0.78 g/ml, even more preferably comprised from 0.70 to 0.75 g/ml.

Thus, following such step, the powder mannitol is densified with respect to step c), and such characteristic makes the filling time of the containers faster.

According to an embodiment, the method comprises a step of:
d) hermetically sealing the filled container of step c), by means of a removable closure element 6.

A single-dose composition according to an embodiment of the present invention comprises or consists of mannitol at an amount comprised from 50 to 200 grams, wherein such mannitol is in powder form.

Such powder preferably has a bulk density comprised from 0.40 to 0.65 g/ml and it comprises powder particles. According to a preferred aspect, a percentage comprised from 90% to 100% by weight of powder particles with a particle size distribution comprised from 1 μm to 500 μm, preferably comprised from 5 μm to 400 μm, more preferably comprised from 10 μm to 300 μm. The aforementioned parameters (amount, density, particle size) must be considered at the end of step c).

As regards the terminology used in this description, the term "single-dose" is used to indicate an amount of a single dose of composition, to be used in a single use as described in greater detail hereinafter.

In this regard, it should be pointed out that the weight of mannitol in the present composition is an unusually high amount (comprised from 50 to 200 g, assuming pure mannitol) for a single dose of composition in the pharmaceutical field, which has posed the inventors of the present invention with new technological challenges. By way of example, the use of a large amount of mannitol has resulted in the unusual use and adaptation of multi-dose containers (i.e., that can be opened and closed several times) to a single use, for single-dose products.

According to an embodiment, the single-dose composition of the present invention consists of an amount comprised from 30 g to 80 g, preferably comprised from 40 g to 70 g, more preferably comprised from 50 g to 60 g of mannitol.

According to another embodiment, the single-dose composition of the present invention consists of an amount comprised from 80 g to 120 g, preferably from 85 g to 115 g, more preferably from 90 g to 110 g, even more preferably from 95 g to 105 g.

According to a further embodiment, the single-dose composition of the present invention consists of an amount comprised from 110 g to 190 g, preferably comprised from 120 g to 180 g, more preferably comprised from 130 g to 179 g, even more preferably comprised from 135 g to 185 g. Preferably, the single-dose composition of the present invention consists of an amount comprised from 140 g to 170 g, preferably comprised from 141 g to 160 g, more preferably comprised from 145 g to 155 g of mannitol.

In this description, the expression "consisting of" is used to indicate a composition in which mannitol is the essentially exclusive component, except for any impurities present therein.

According to an embodiment, the single-dose composition is devoid of pyrogenic substances and/or devoid of excipients.

More specifically, avoiding the use of excipients which facilitate densification and/or the flow of mannitol into the container, but which simultaneously could have slowed down the dissolution thereof, was considered a necessity and an attention toward the patient who, following ingestion of the mannitol composition previously dissolved in water, is subjected to an almost complete emptying of the bowel, in order not to risk administering any unnecessary and foreign component which could interfere with the practices for the pre-treatment and distension of the colon walls in order to perform a correct colonoscopy. According to another embodiment, mannitol has a percentage by weight comprised from 97% to 100%, preferably comprised from 98% to 100% or comprised from 99% to 100%, or of 100%, with respect to the total weight of such composition. By way of example, possible components other than mannitol (when present, at an amount less than 3% by weight with respect to the total weight of the composition) could comprise substances related to mannitol, such as other polyalcohols, for example sorbitol.

According to a preferred embodiment, mannitol has a percentage by weight of 99.5%, of 99.6%, of 99.7%, of 99.8%, of 99.9% or of 100% with respect to the total weight of such composition. Preferably, the mannitol contained in the composition is of a pharmaceutical grade.

It should be observed that, in each range of values mentioned in this specification, the extremes of the range are to be deemed within the range (unless the context clearly indicates otherwise), same case applying to any intermediate value between the extremes, although not explicitly stated numerically.

As regards the terms "in powder form", this expression is used to indicate mannitol in finely divided, pulverulent form, comprising a plurality of powder particles.

With regard to the expression "particle size distribution" (PSD), this term is used indicate the statistical dimensional distribution curve of the powder particles.

According to an embodiment, the powder particle size distribution could be as in Table 1 below:

TABLE 1

| Range | Particles % |
|---|---|
| <100 μm | 25.87% |
| 180-100 μm | 54.88% |
| 250-180 μm | 16.59% |
| 365-250 μm | 0.96% |
| 500-365 μm | 1.27% |
| 600-500 μm | 0.43% |
| ≥600 μm | 0.59% |

According to an embodiment, the powder particles could be substantially spherical-shaped.

This means that the particle size distribution discussed in this description could be a "particle size diameter" with the same characteristics described, for example comprised from 1 μm to 500 μm, preferably comprised from 5 μm to 400 μm, more preferably comprised from 10 μm to 300 μm, even more preferably comprised from 15 μm to 250 μm, without prejudice to any variability (±) comprised from 1% to 15% (as discussed hereinafter).

As concerns the embodiments that provide for "substantially spherical" powder particles, it should be observed that the sphericity parameter is defined by the ratio between the outer surface of a powder particle and the outer surface of an equivalent sphere (i.e. a sphere of the same volume as the powder particle).

In such context, a powder particle is deemed to be "substantially spherical" if it has a sphericity parameter comprised from 1 to 1.3, preferably comprised from 1 to 1.2, more preferably comprised from 1 to 1.15, even more preferably comprised from 1 to 1.1 or comprised from 1 to 1.05.

As regards the bulk density outlined above, in particular the poured bulk density, such parameter is measured according to the European Pharmacopoeia reference standard (Ph. EUR.), current edition 2.2.42, in force at the priority date of this patent application.

In the context of the present invention, the expression "bulk" implies that the powder density value is calculated in a manner formally analogous to an absolute density (such as for a solid body or for a liquid). However, since a powder has empty inter-particle spaces, the total volume occupied by the powder (i.e. its outer bulk), thus including the inter-particle spaces between the various particles, should be taken into account when evaluating bulk density.

More precisely, according to the aforementioned standard, a 100 ml class A graduated flask is filled and brought to volume with the powder particles, after which the bulk density is calculated as the ratio between the weight of the powder inside the flask and the volume (100 ml) occupied by that weight of the powder particles.

According to an embodiment, the bulk density of the mannitol powder inside the container may be comprised from 0.42 g/ml to 0.64 g/ml, preferably from 0.50 g/ml to 0.62 g/ml, more preferably from 0.56 g/ml to 0.60 g/ml, even more preferably comprised from 0.57 g/ml to 0.59 g/ml.

According to another embodiment, the bulk density of mannitol powder is 0.58 g/ml.

According to an embodiment, a method that can be used for analysing the particle size distribution is discussed hereinafter: 100 g of mannitol powder are screened using 600 μm, 500 μm, 355 μm, 250 μm, 180 μm and 100 μm ASTM series sieves. All sieves except for the 100 μm sieve come from GIULIANI TECNOLOGIE S.r.l. (Via Centallo 62/18, 10156 Turin, Italy; https://www.giuliani.it/setacci-sieves). The 100 μm sieve comes from Retsch GmbH (Retsch-Allee 1-5, 42781 Haan, Germany;). https://www.retsch.com/products/sieving/ Such sieves were connected to a vibrating screen made by RMU-Resistenze Meccaniche Unificate serial n° 42280, at an intensity of 10, for 13 minutes. Following screening, a particle size profile of the mannitol powder is constructed. Regarding this, see for example the particle size profiles of Table 2 or of Table 3.

As concerns the powder particle size distribution, it should be observed that the particle size distribution will be comprised from 1 μm to 500 μm, unless there is a variability (±) comprised from 1% to 15%, preferably comprised from 1% to 10%, more preferably comprised from 1% to 5%, with respect to the upper limit of the range of 500 μm (or 400 μm, 300 μm, 250 μm according to other embodiments).

According to a particularly preferred embodiment, the powder particles have a particle size distribution comprised from 1 μm to 250 μm, without prejudice to a possible variability (±) comprised from 1% to 15%, preferably comprised from 1% to 10%, more preferably comprised from 1% to 5%, with respect to the upper limit of the range (250 μm).

According to an advantageous embodiment, the aforementioned single-dose composition, according to any one of the illustrated embodiments, is a single-dose composition for use in the treatment of the constipation, or for use as a purgative to be administered to a patient prior to a colonoscopy examination.

A container 1 according to an embodiment contains a single-dose composition—according to any one of the preceding claims—in a container compartment hermetically sealed by a removable closure element 6.

The aforementioned objectives are also achieved through a heat-sealed pouch, preferably a single-dose heat-sealed pouch, containing a single-dose composition—according to any of the previous embodiments —in a container compartment 4 sealed closed by a removable or tear-off closure element, in to which said heat-sealed pouch is made of a polymeric material which may possibly also be compostable according to the UNI EN 13432 or ASTM D6400 standard.

In other words, such container 1 preferably forms the primary casing for mannitol in powder form, with which the powder particles are directly at contact.

It should be observed that the expression "hermetically" is used to indicate the ability to at least prevent the powder from leaking out from the container compartment and/or from the inner compartment discussed hereinafter. Preferably, the expression "hermetically" in the context of the dissolving container 30 entails a substantially airtight sealing of the inner compartment 26 of such dissolving container 30, in order to obtain the single-dose solution.

As regards the UNI EN 13432 or ASTM D6400 standard mentioned above, this standard is intended in the version valid at the priority date of this patent application.

Preferably, the compostable polymeric material comprises or, alternatively, consists of at least one polylactic acid (PLA) film.

Figure 1:
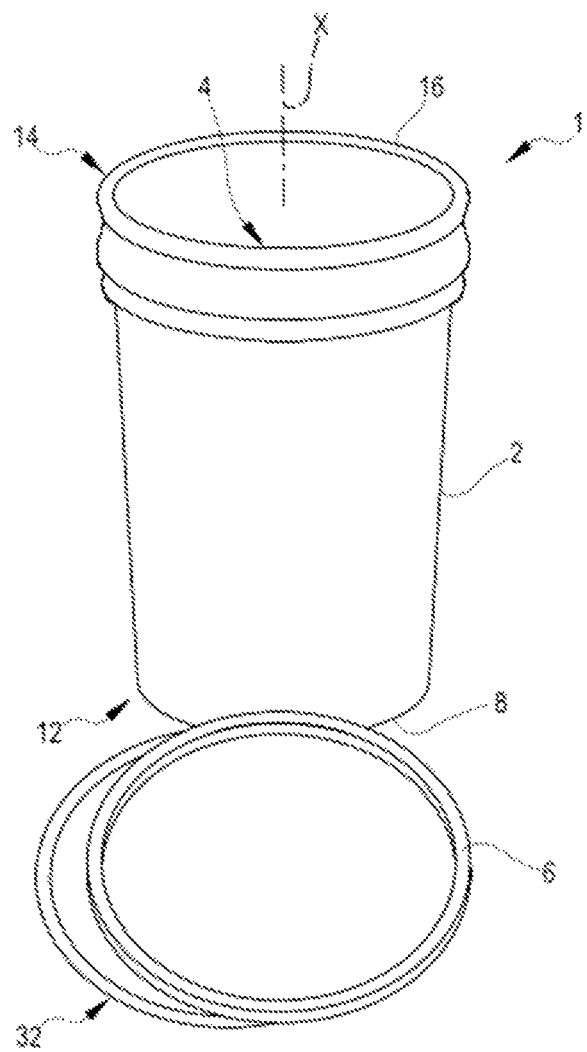
FIG. 1 shows a container subject of the present invention, according to a first embodiment, wherein the closure element is spaced from the container compartment.

With reference for example to the embodiment of FIG. 1, the container 1 comprises a first lateral wall 2 which extends around a first main extension axis X so as to delimit the container compartment 4.

According to an embodiment, the first lateral wall 2 is connected to a first bottom wall 8 at a first axial end 12 of the container 1 and, at an opposite second axial end 14, it delimits at least one opening 16 for access to the container compartment 4.

According to another embodiment, the container 1 or the first lateral wall 2 could be substantially cylindrical-shaped or truncated-cone-shaped.

According to a further embodiment, the container 1, or the first lateral wall 2 and the optional first bottom wall 8, could be made of a polymeric material, preferably polyethylene (preferably high-density polyethylene; HDPE) or polypropylene.

According to an embodiment, the closure element 6 can be connected to the first lateral wall 2, in particular at the second axial end 14 of the container 1, so as to hermetically seal the container compartment 4.

According to another embodiment, the closure element 6 is made of a more flexible material with respect to the material that the container or the first lateral wall 2 is made of, said material being preferably polymeric such as low-density polyethylene (LDPE).

According to a further embodiment, the closure element 6 and the container 1 (or the first lateral wall 2 thereof) could be joined by a tamper-proof seal 32, preferably annular-shaped and/or in the form of a flange.

Therefore, according to such embodiment, before accessing the single-dose composition it will be necessary to tear and/or remove the tamper-proof seal 32, and to remove the closure element 6.

According to one embodiment, the tamper-proof seal 32 could be designed so as to act as a stirrer, following the tearing or removal thereof. More precisely, the torn or removed seal could be elongated-shaped, so as to be inserted into the container compartment 4 and/or into the inner compartment 26 and be actuated manually in order to facilitate the dissolution of the mannitol powder.

Preferably, the polymeric material of the container 1 (or, of the first lateral wall 2 and of the optional first bottom wall 8) is non-identical/different with respect to the polymeric material that the closure element 6 is made of.

Preferably, the polymeric material of the closure element 6 could be polyethylene (preferably low-density polyethylene; LDPE).

In accordance with an embodiment, the heat-sealed pouch, preferably a heat-sealed closed pouch, preferably having 4 ends (4 sides, perimeter end) heat-sealed, for example in a square or rectangular shape. Said heat-sealed envelope (FIG. 9; 1) could comprise or, alternatively, consist of a pair of envelope walls made from said polymeric material or in another specific polymer compostable in the form of a film of material, said envelope walls being heat-sealed. welded together along the perimeter through one or more heat-sealing areas (FIG. 9; 2). The embodiment of FIG. 9 shows the envelope wall facing upwards (the opposite wall being hidden from view), polygonal, preferably square or rectangular. The heat-sealed external part 6 in FIG. 9 also represents a closing element which can be removed using for example cutting means such as a shears.

According to an embodiment, the container 1 (preferably a single-dose container, or a heat-sealed bag on the single-dose sides), delimits the container compartment 4, said container compartment 4 comprising a first volume fraction and a second volume fraction. Preferably, at the end of step c), the first volume fraction 18 is occupied by the single-dose composition, and the second volume fraction 20 of such compartment is devoid of the aforementioned composition. More precisely, the second volume fraction 20 could contain a gas, preferably air or at least an inert gas.

In other words, above a vacant surface 22 of the single-dose composition 1 in the container compartment 4 there is a space devoid of mannitol corresponding to the second volume fraction 20.

According to another embodiment, the first volume fraction is equal to or greater than about half of a total internal volume of the container compartment 4.

According to a further embodiment, the first volume fraction is about two-thirds of the total internal volume of the container compartment 4, the second volume fraction being consequently one-third of the total internal volume of such compartment 4.

A kit according to an embodiment of the present invention comprises the container 1 according to any one of the preceding claims, a dissolving container 30 at least partially permeable to light, and a funnel 24 for transferring the single-dose composition from the container 1 to the dissolving container 30.

It should be observed that, the expression "at least partially permeable to light", is used to indicate a dissolving container 30 with at least one portion 36 at least partly transparent (for example: a completely transparent container, or a container with at least one transparent portion 36), so as to allow to see—from the outside—at least one part of an inner compartment 26 of such container, in particular without the need to open the latter. This expression will also include a container comprising at least one pair of transparent portions 36, for example diametrically opposite or contralateral.

The at least partial permeability to light has a double utility in the context of the present invention: on the one hand, seeing the inner compartment 26 allows to establish the complete dissolution of mannitol. On the other hand, in some embodiments, such characteristic allows the introduction of a water volume appropriate for dissolution, or in any case, to establish that the water volume already present in the container is sufficient for a quantitative dissolution of mannitol.

The expression "appropriate water volume" therefore refers to the volume of water present or that can be introduced into the inner compartment, appropriate for fully dissolving the mannitol in powder form.

According to a first embodiment, contained in the dissolving container 30 is a water volume appropriate to completely dissolve the single-dose composition contained in the container 1 or in the heat-sealed envelope.

According to a second embodiment, the dissolving container 30 comprises a level indicator 28 for a water volume that can be introduced (that is, to be introduced) into the dissolving container 30 and appropriate to completely dissolve the single-dose composition contained in the container 1 or in the heat-sealed envelope.

In other words, in these two last embodiments the dissolving container 30 could already be filled with the appropriate water volume, or such container 30 could initially be empty but provided with a level indicator 28 so that a user can, on his own account, introduce the appropriate water volume, specifically without making mistakes.

It should be observed that the term "water" has no particular limitations in the present description.

According to an embodiment, the water could comprise or consist of deionised water, demineralised water, mineral water (preferably non-carbonated), or mains water.

As a matter of fact, it has been found that any salts previously dissolved in water have no negative effects on the solvation of mannitol, which is surprising since the salts already dissolved in water should compete with mannitol due to the solvation capacity of water, and they should increase the time required for the dissolution of mannitol powder.

On the other hand, with the mannitol powder according to the present invention dissolution was not observed to slow down, although the dissolution kinetics justifying the absence of slowing remain yet to be clarified.

According to an embodiment, the water required for the dissolution of mannitol is at a substantially neutral pH (pH 7.0±0.2), or it is weakly basic, preferably at pH 8.0±0.5.

With regard to the level indicator 28, in an embodiment such indicator could comprise or consist of a sign, a notch, a line or an alphanumeric character arranged on the dissolving container 30, in particular at a window or portion 36 at least partially permeable to light.

More precisely, a second lateral wall 34 of the dissolving container could delimit such window 36.

According to another embodiment, the second lateral wall 34 of the dissolving container could delimit at least two windows 36, for example contralateral or diametrically opposite, specifically so as to allow a backlit verification of the complete dissolution of mannitol.

Figure 8:
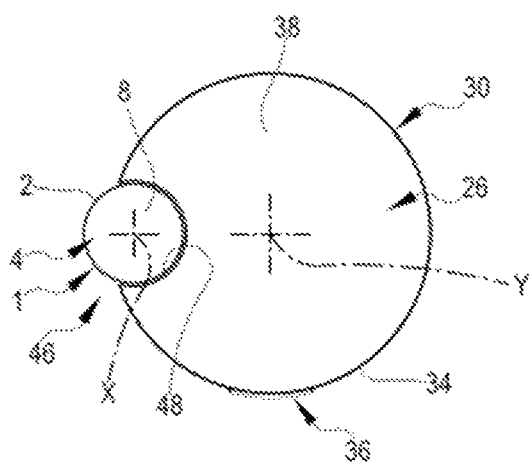

With reference for example to the embodiment of FIG. 8, the dissolving container 30 comprises the second lateral wall 34 which extends around a second main extension axis Y so as to delimit the inner compartment 26.

According to an embodiment, the second lateral wall 34 is connected to a second bottom wall 38 at a first axial end 40 of the container 30 and, at an opposite second axial end 42, it delimits at least one opening 44 for access to the inner compartment 26.

As regards the characteristics and materials that can be used for the dissolving container 30, the preferred or accessory characteristics mentioned in relation to the container 1 shall apply mutatis mutandis.

According to an embodiment, the ratio between the weight of the mannitol contained in the container 1 or in the heat-sealed envelope and the water volume contained or that can be introduced up to the level indicator 28 in the dissolving container 30 are mutually selected so as to obtain—at a temperature of 25° C. and at ambient pressure—a concentration of mannitol in aqueous solution comprised from 0.05 g/ml to 0.213 g/ml, preferably comprised from 0.1 g/ml to 0.19 g/ml.

According to an embodiment, the container 1 or the heat-sealed envelope is shape-coupled to the, or it is at least partially nested in the dissolving container 30

According to another embodiment, the dissolving container 30 could define a coupling seat with the, or a housing seat 46 of the container 1 or the heat-sealed envelope.

By way of example, the coupling seat or the housing seat 46 could comprise a recess 48 which at least partly houses the container 1 or the heat-sealed envelope, for example partially, in a predominant or substantially complete manner.

Figure 7:
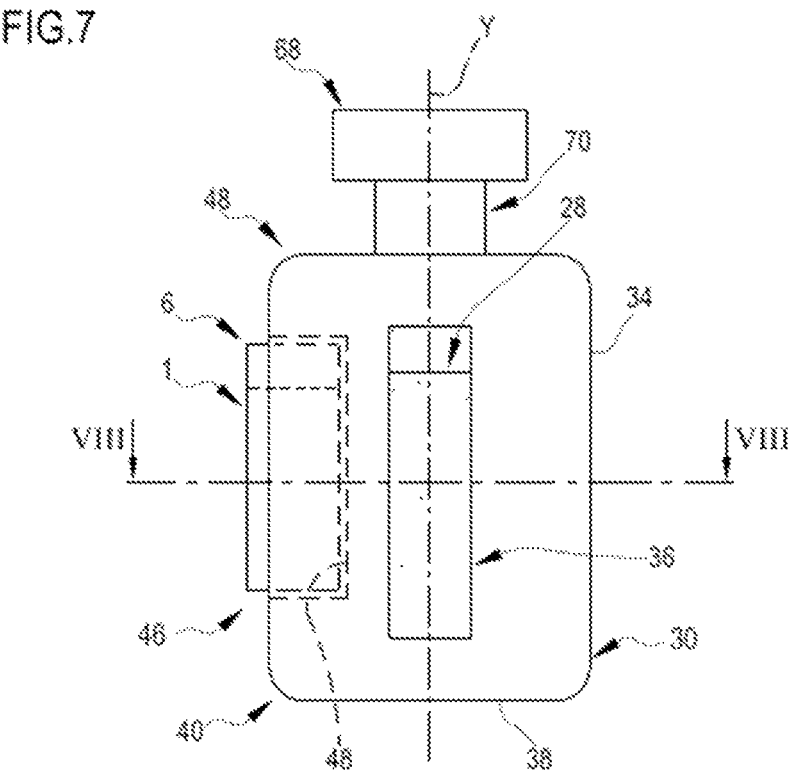
FIGS. 7, 8 show a container and dissolving container assembly according to another embodiment, respectively in a lateral view and in a cross section at the plane VIII-VIII schematised in FIG. 7.

With reference for example to the variant of FIGS. 7 and 8, the second lateral wall 34 is shaped so as to identify the recess 48, being for example designed with a concavity toward the external of the dissolving container 30 (i.e. on the opposite side with respect to the inner compartment 26).

According to an embodiment, when the container 1 or the heat-sealed envelope is associated with the coupling seat or with the housing seat 46, the main extension axes X, Y are substantially parallel to each other and advantageously non-coincident.

According to another embodiment, at least one second lateral wall of the dissolving container 30 is flexible so that an inner compartment 26 of such container is expandable from an at least partially collapsed configuration to an expanded configuration.

According to a first example, the second lateral wall 34 could comprise at least one bellows-like portion 50 so as to allow conversion between the aforementioned configurations.

More precisely, the second lateral wall 34 could comprise an axial alternation (with respect to the second main extension direction Y) of outer tubular or annular portions 52 arranged side by side and connected to inner tubular or annular portions 54 which form one or more bellows-like portions 50.

In this manner, in the at least partially collapsed configuration, the inner tubular or annular portions 54 are housed (specifically: radially) at least partly in the outer tubular or annular portions 52, so that the volume of the inner compartment 26 is smaller.

However, when the inner compartment 26 is converted into the expanded configuration (for example by pulling on the axial ends 40, 42 of the container), the inner tubular or annular portions 54 move axially alongside the outer tubular or annular portions 52, so that the volume of the inner compartment 26 is greater (at least with respect to the at least partially collapsed configuration).

According to a second example, the second lateral wall 34 could be made of at least one pair of material films 56, 58 joined to each other (for example sealed), for example at the respective peripheral portions 60, so as to allow conversion between the aforementioned configurations.

According to such variant, the inner compartment 26 is advantageously enclosed at least by such pair of material films 56, 58.

Advantageously, the two or more material films 56, 58 are joined to each other so as to form a self-supporting bottom 60 (for example a substantially flat bottom) in the expanded configuration.

As regards the funnel 24, it comprises a powder-loading portion 64 and a powder-discharge portion 66, the through-flow section through such funnel being tapered at the powder-loading portion 64 toward the powder-discharge portion 66.

According to an embodiment, the powder-loading portion 64 could be truncated-cone or truncated-pyramidal-shaped.

According to another embodiment, the powder-discharge portion 66 could be substantially tubular, or truncated-cone or truncated-pyramidal-shaped.

In a possible embodiment, the kit according to any one of the preceding embodiments is arranged in a secondary, preferably protective, housing.

Also described herein is a method for using the kit, according to any of the embodiments illustrated above. Such process comprises the following steps:
  i) removing the closure element from the container 1 or from the heat-sealed envelope (e.g. tear a portion of the heat-sealed envelope);
  ii) transferring the single-dose composition from the container 1 to the dissolving container 30 using the funnel 24;
  iii) completely dissolving the mannitol powder in the water volume thus obtaining a single-dose solution.

According to an embodiment, the transfer step ii) could comprises the following sub-steps:
  ii.a) first pouring at least one part of the appropriate water volume into the container 1 or in the heat-sealed envelope, so as to pre-dissolve the mannitol powder;
  ii.b) subsequently transferring the mannitol pre-dissolution of sub-step ii.a) into the dissolving container 30. For example, sub-step ii. a) could comprise at least one (pre-)shaking and/or stirring operation. The term "(pre-)shaking" is used to indicate a pre-shaking and/or shaking operation.

As a matter of fact, mannitol is a poorly flowing powder, hence this embodiment allows to avoid annoying clogging of the funnel due to the increased flowability conferred by water.

According to an embodiment, the container 1 or the heat-sealed envelope could comprise a further level indicator. In this manner, during sub-step ii. a), a part of the water volume could be poured into the container compartment 4 until it corresponds with such further level indicator.

In quantitative terms, according to an embodiment, the single-dose solution of step iii) could contain about 50 g of mannitol in at least 350 ml of water (preferably about 50 g of mannitol in 500 ml of water).

According to another embodiment, the single-dose solution of step iii) could contain about 100 g of mannitol in at least 600 ml of water (preferably about 100 g of mannitol in 700 ml of water).

According to a further embodiment, the single-dose solution of step iii) could contain about 150 g of mannitol in at least 800 ml of water (for example about 150 g of mannitol in 900 ml of water).

In any case, the principles which should be observed in the determination of the amount of mannitol powder and the appropriate water volume are: a) the desired efficacy for the single-dose solution; and b) not exceeding the saturation concentration at the solution consumption temperature.

Preferably, the dissolving step iii) could comprise the following sub-steps:
  iii.a) sealing (for example closing) the dissolving container 30;
  iii.b) shaking the dissolving container 30 of sub-step iii.a) until, using a portion 36 of said container at least partially permeable to light, the precipitates/sediments in the single-dose solution disappear.

With regard to sub-step iii. a), the dissolving container could comprise a cap or closure member 68, which can be reversibly connected to the dissolving container 30, for example to a container neck 70 of the latter.

By way of example, the cap or closure member 68 and the dissolving container 30 (or container neck 70) could be provided with complementary threaded means 72.

As regards the execution times of step iii. b), in an embodiment the shaking could be carried out—for a mass of single-dose composition comprised from 50 to 100 g—for a time comprised from 15 seconds to 2 minutes.

With reference to FIG. 9, illustrated hereinafter is a filling device 74 for implementing the filling method illustrated in any of the preceding embodiments.

A coherent mass of mannitol in powder form is initially contained in a coherent mass container 76.

A first conveying duct 78 is functionally connected to (for example inserted into) the coherent mass container 76 so that the coherent mass can be displaced or made to flow toward a drum centrifugal sieve shaker 80. The direction of displacement of the coherent mass is identified by the arrow S1 in FIG. 9.

For example, such displacement could be carried out through suctioning means 82 arranged along the first conveying duct 78, and fluidly connected to the drum centrifugal sieve shaker 80 by means of a second conveying duct 84.

According to an embodiment, the filling device 74 could comprise a compressed air source 96, connected to the drum centrifugal sieve shaker 80 by means of an air duct 98. In this manner, a flow of compressed air—identified by the displacement direction S2 in FIG. 9—is capable of further pushing the coherent mass and the broken-up mass through the drum centrifugal sieve shaker 80.

With reference to FIG. 10, an embodiment of the aforementioned sieve shaker 80 comprises a sieve shaker casing 86 inside which a substantially tubular-shaped mesh 88 and a sieve shaker drum 90 are housed.

The mesh 88 is provided with a plurality of radial openings 94 configured to place a cylindrical compartment 92 circumscribed by the mesh in communication with an interspace 102 delimited between said mesh 88 and the sieve shaker casing 86.

The sieve shaker drum 90 is housed in the cylindrical compartment 92 of the mesh 88, rotatably around a rotation axis R, with respect to the mesh 88. In the illustrated embodiments, the rotation axis R is a substantially vertical axis.

For example, the sieve shaker drum 90 could comprise one or more drum blades 104. In the illustrated embodiment, the at least one drum blade could have an axial orientation with respect to the rotation axis R.

The coherent mass entering into the centrifugal drum sieving unit 80 through the second conveying duct 84 will then reach the cylindrical compartment 92. Under the action of the sieve shaker drum 90 (for example by means of the drum blade 104), such mass is forced through the radial openings 94 toward the interspace 102, thus orienting the powder particles all along the same direction, packing such particles. When traversing the radial openings 94, the coherent mass is transformed into broken-up mass.

The broken-up mass then reaches a discharge opening 100, delimited by the sieve shaker casing 86, for example under the action of the force of gravity or by virtue of the thrust received from the flow of compressed air.

The broken-up mass can then pass through the discharge opening 100, and be used to fill the containers 1.

Examples will be provided hereinafter by way of non-limiting example.

EXAMPLES

Example 1: Characterisation of Mannitol

The specifications of a mannitol that can be used according to the present invention are shown in Table 2 below. The tests were conducted according to the European Pharmacopoeia reference standards in force at the priority date of the present application.

The tested product is a pharmaceutical grade mannitol named Pearlitol® PF, cod. 050054, manufactured by Faravelli Group S.p.A.

TABLE 2

| Parameters | Specifications |
|---|---|
| Identity (IR) | Test passed |
| D-Mannitol assay (HPLC) | 97.0-102.0% |
| Appearance of the solution | Clear colourless |
| Melting point | 165-170° C. |
| Reducing sugars | 0.1% max |
| Impurity A: D-Sorbitol | 2.0% max |
| Sum of other impurities (B and C) | 2.0% max |
| Impurities not specified | 0.10% max |
| Total impurities | 2.0% max |
| Heavy metals | ≤5 ppm |
| Nickel | 1 ppm max. |
| Loss on drying (at 105° C., up to constant weight) | ≤0.50% |
| Total aerobic microbial count | 100 CFU/g max |
| Total yeast and muold count | 100 CFU/g max |
| *Escherichia coli* | absent in 10 g |
| *Salmonella* | absent in 10 g |

Example 2: Particle Size Profile

The particle size profile of three different samples, distinguished by the batch number in Table 3 below, was verified before and after sieving performed to uniform the in-line filling of containers on industrial scale

TABLE 3

| | | Batch 1803711 | | Batch 1803848 | | Batch 1804020 | |
|---|---|---|---|---|---|---|---|
| Sieve | Range | Before | After | Before | After | Before | After |
| Sediment | <100 μm | 28.75% | 33.54% | 26.96% | 27.58% | 29.40% | 28.35% |
| 100 μm | 180-100 μm | 51.46% | 49.68% | 52.38% | 54.88% | 55.08% | 52.04% |
| 180 μm | 250-180 μm | 9.97% | 13.09% | 16.55% | 14.91% | 12.75% | 15.54% |
| 250 μm | 365-250 μm | 1.00% | 1.57% | 1.52% | 1.06% | 0.98% | 0.88% |
| 365 μm | 500-365 μm | 0.85% | 1.46% | 0.98% | 1.15% | 0.85% | 0.92% |
| 500 μm | 600-500 μm | 0.25% | 0.66% | 0.38% | 0.42% | 0.23% | 0.26% |
| 600 μm | ≥600 μm | 7.72% | 3.16% | 1.24% | 1.11% | 0.85% | 0.11% |

From the previous table it can be observed that the sieving has a break-up effect with respect to the coarser grain size fractions (≥600 μm), whose fragmentation enriches by various percentages the finer grain size fractions 100-250 μm.

The grain size of the single dose composition in a further productive batch is summarised in Table 4 below, whereas the last column on the right shows the percentage by weight of each of the fractions identified in the central column:

TABLE 4

| Sieve | Range | Batch P01/18 |
|---|---|---|
| Fondo | <100 μm | 25.87% |
| 100 μm | 180-100 μm | 54.88% |
| 180 μm | 250-180 μm | 16.59% |
| 250 μm | 365-250 μm | 0.96% |
| 365 μm | 500-365 μm | 1.27% |
| 500 μm | 600-500 μm | 0.43% |
| 600 μm | ≥600 μm | 0.59% |

Example 3: Dissolution Study

The solubility of the mannitol powder was then studied in the following three types of non-carbonated commercial waters:
Sangemini: PH at source 6.2;
Antica Fonte Boario: PH at source 7.0;
Panna Toscana: pH at source 8.0.
The results obtained are shown in Table 5 below:

TABLE 5

| CODE | MANNITOL PHARMA | VOLUME | CONCENTRATION | DISSOLUTION TIME | | |
|---|---|---|---|---|---|---|
| | | | | Sangemini (pH 6.2) | Boario (Ph 6.2) | Panna (pH 8.0) |
| 430280 | 50 g | 500 ml | 0.1 g/ml | 28 sec | 40 sec | 48 sec |
| 430281 | 100 g | 700 ml | 0.14 g/ml | 1 min 36 sec | 1 min 2 sec | 1 min 29 sec. |
| 430282 | 150 g | 900 ml | 0.17 g/ml | 6 min 15 sec | 6 min 52 sec | 3 min 27 sec |

A difficulty of dissolving 150 g of mannitol in 900 ml of water can be deduced from the table above: complete dissolution takes more than 6 minutes for water with weakly acidic or neutral pH, but this time is substantially half as much under weakly basic pH conditions.

Such circumstance is odd and still unexplained in the case of the most critical amount to be dissolved, 150 g: the experimental evidence shows that a slightly basic pH accelerates the dissolution times, even if it has no theoretical assumption since mannitol (itself slightly basic in solution), is expected to dissolve better at slightly acidic pH.

However, an acceleration of dissolution as a function of pH values cannot be observed for samples with 100 g or 50 g of mannitol.

Example 4: Container Filling Procedure

Mannitol powder is a poorly flowing powder, which has a certain tendency, just like all fine powders, to agglomerate under pressure. A drum centrifugal sieve shaker, through which the whole coherent mass of the powder particles—having a poured bulk density of about 0.60 g/ml—was passed through before the pre-metering mixing in the container, was used with the aim of breaking up any large lumps of powder.

A mesh was used with a clear span of 3 mm, much larger than the average particle size or diameter of mannitol (for example at least 90% with a diameter comprised from 1 μm to 250 μm, which—expressed in mm—are equivalent to 0.001 mm and 0.250 mm respectively).

Usually this step further reduces the density of the powders which quickly impact against the edges of the meshes of the mesh, causing a decrease in density due to a reduction in size and an increase in the disorderly arrangement of the particles, which—based on past evidence—can increase the volume of the material even by as much as 30%.

It has now surprisingly been observed that the use of such a sieve shaker allows to accelerate the process of the in-line filling of containers up to 50%, reducing the downtime and the onset of waste due to faulty filling.

Given the size of the mannitol particles, the passing through a mesh much larger than previously indicated would not be effective in reducing the size thereof, but it shows to be extremely useful in orienting and packing the powder particles, allowing to obtain—in a short through-passing—a much greater transient density, of about 0.73 g/ml, measured in the laboratory, which considerably facilitates a faster descent of the powder into the disposable container.

This behaviour seems to stem from the orientation of the particles that pack better together. Furthermore, with a material already densified at the time of metering in the disposable container, this allows to reduce the metering times and to use smaller bottles, without further settling in the volume which could inevitably occur as the filled disposable container moves toward the labelling.

Example 5: Dissolution Study as a Function of the Average Particle Size and Density of the Mannitol Powder Used The dissolution rate of two types of powdered mannitol was compared:
Type 1: a mannitol object of the present invention (Pearlitol® PF; referred to in Example 1) in the form of a powder with an apparent density ranging from 0.40 to 0.65 g/ml and whose particle size profile is that of Table 6 below:

TABLE 6

| Sieve (μm) | Tare (g) | Gross (G) | Net (g) | % | RANGE |
|---|---|---|---|---|---|
| 600 | 441.41 | 442.95 | 1.54 | 1.539538139 | >600 |
| 500 | 438.42 | 438.65 | 0.23 | 0.229931021 | 600-500 |
| 355 | 395.27 | 396.64 | 1.37 | 1.369589123 | 500-355 |
| 250 | 404.29 | 405.19 | 0.9 | 0.899730081 | 355-250 |
| 180 | 399.1 | 407.24 | 8.14 | 8.137558732 | 250-180 |
| sediment (<180) | 389.34 | 477.13 | 87.79 | 87.7636709 | <100 |
| total | | | 98.43 | 98.40047986 | |

Therefore, in Type 1 mannitol about 96.6% by weight of the dust particles has an average particle size ranging from 1 μm to 500 μm;

Type 2: a reference mannitol (Pearlitol® 500 DC, marketed by Roquette) in the form of a powder with an apparent density of about 0.673/0.683 g/ml (values obtained in two different measurements) and in which 100% by weight dust particles have an average particle size greater than 500 μm, in particular from 520 μm to 850 μm. This size of the dust particles was obtained through subsequent sieving operations.

From an operational point of view, the dissolution tests were carried out following the reference analytical specifications of the finished product: "Solve the prescribed quantity of product powder in the indicated quantity of purified water. Manually stir with a stick until the dissolution is complete. Measure the time needed to complete solubilization." The distilled water used had a temperature of about 19.4° C. and the tests were carried out at atmospheric pressure (1 atm), and the stirring is of the manual type carried out by an expert analyst. The results of this dissolution study are reported in Table 7 below.

TABLE 7

| Type | Medium particle size | Weight of solubilized powder (in g.) | Volume of water (in ml) | Solubilization time min | sec |
|---|---|---|---|---|---|
| 1 | <500 μm | 50 | 500 | 0 | 44 |
| 1 | <500 μm | 150 | 1000 | 0 | 51 |
| 2 | >500 μm | 50 | 500 | 3 | 44 |
| 2 | >500 μm | 150 | 1000 | 7 | 40 |

From the previous Table 7 it can be observed how—in both the tests carried out—the mannitol in the form of powder object of the present invention has a dissolution rate below the minute. All things being equal, Type 2 mannitol powder (with higher average density and particle size) takes more than 3 minutes and more than 7 minutes to dissolve.

Example 6: Stability Data of Mannitol in Powder Form Object of the Present Invention The stability of the mannitol in the form of powder object of the present invention was tested, housed inside a heat-sealed envelope in compostable material. 50 grams of said powder were stored for 6 months at 40° C./75% RH (Test 1) and for 6 months at 25° C./60% RH (Test 2). Checks were made of the parameters indicated in Tables 8 and 9 following the times T0-T6 identified as: T0=moment of insertion of the air-conditioned environment, T1=after one month from the moment T0, T2=after two months from the moment T0, T3=after three months from the time T0, T4=after four months from the time T0, T5=after five months from the time T0, T6=after six months from the time T0.

TABLE 8

| Accelerated stability 40° C./75% RH | MONTHS | | | | | | Batch P19001 |
|---|---|---|---|---|---|---|---|
| | T0 | T1 | T2 | T3 | T5 | T6 | SPECIFICATIONS |
| Appearance | C | C | C | C | C | C | Crystals or powder |
| Colour | C | C | C | C | C | C | White or almost white |
| Appearance of the solutions (1 sachet in 500 ml) | C | C | C | C | C | C | Clear and colourless solution |
| Appearance of the soltions (2 sachet in 750 ml) | C | C | C | C | C | C | Clear and colourless solution |
| Appearance of the soltions (3 sachet in 1000 ml) | C | C | C | C | C | C | Clear and colourless solution |
| Particle size (<600 μm) | 100 | 100 | 99 | 100 | | | ≥85% (only for information) |
| Average weight | 50.9 | 50.7 | 50.9 | 50.6 | 51.0 | 50.8 | 50.0-55.0 g/sachet |
| D-Mannitol IR ID | P | P | P | P | P | P | Positive |
| D-Mannitol HPLC ID | P | P | P | P | P | P | Positive |
| D-Mannitol assay HPLC | 99.1 | 98.7 | 99.6 | 99.4 | 99.4 | 98.8 | 95.0-102.0% |
| Impurity A: D-sorbitol | 0.8 | 0.8 | 0.7 | 0.8 | 0.6 | 0.7 | ≤2.0% |
| Sum of impurity B (maltitol) and C (isomalto) | <0.05 | 0.1 | <0.05 | <0.05 | 0.1 | <0.05 | ≤2.0% |
| Unspecified impurities | <0.05 | <0.05 | <0.05 | <0.05 | <0.05 | <0.05 | ≤0.10% |
| Total Impurities | 0.8 | 0.8 | 0.7 | 0.9 | 0.7 | 0.7 | ≤2.0% |
| Loss on drying | 0.1 | <0.05 | <0.05 | 0.1 | <0.05 | 0.1 | ≤0.05% |
| Total aerobic microbial count | <10 | | | | <10 | <10 | ≤$10^3$ cfu/g |
| Total yeasts and moulds count | <10 | | | | <10 | <10 | ≤$10^2$ cfu/g |
| *Escherichia coli* | A | | | | A | A | Absence/g |

TABLE 9

| Long term stability 25° C./60% RH | MONTHS | | | | | | | | | | Batch P19001 |
|---|---|---|---|---|---|---|---|---|---|---|---|
| | T0 | T1 | T2 | T3 | T5 | T6 | T9 | T12 | T18 | T24 | SPECIFICATIONS |
| Appearance | C | C | C | C | C | C | | | | | Crystals or powder |
| Colour | C | C | C | C | C | C | | | | | White or almost white |
| Appearance of the solutions (1 sachet in 500 ml) | C | C | C | C | C | C | | | | | Clear and colourless solution |
| Appearance of the solutions (2 sachet in 750 ml) | C | C | C | C | C | C | | | | | Clear and colourless solution |
| Appearance of the solutions (3 sachet in 1000 ml) | C | C | C | C | C | C | | | | | Clear and colourless solution |
| Particle size (<600 μm) | 100 | 100 | 100 | 100 | | | | | | | ≥85% (only for information) |

TABLE 9-continued

| Long term stability 25° C./60% RH | T0 | T1 | T2 | T3 | T5 | T6 | T9 | T12 | T18 | T24 | Batch P19001 SPECIFICATIONS |
|---|---|---|---|---|---|---|---|---|---|---|---|
| Average weight | 50.9 | 51.3 | 51.1 | 51.2 | 52.0 | 51.0 | | | | | 50.0-55.0 g/sachet |
| D-Mannitol IR ID | P | P | P | P | P | P | | | | | Positive |
| D-Mannitol HPLC ID | P | P | P | P | P | P | | | | | Positive |
| D-Mannitol assay HPLC | 99.1 | 98.7 | 99.7 | 99.5 | 99.1 | 98.9 | | | | | 95.0-102.0% |
| Impurity A: D-sorbitol | 0.8 | 0.8 | 0.7 | 1.0 | 0.7 | 0.7 | | | | | ≤2.0% |
| Sum of impurity B (maltitol) and C (isomalto) | <0.05 | 0.1 | <0.05 | 0.1 | 0.1 | <0.05 | | | | | ≤2.0% |
| Unspecified impurities | <0.05 | <0.05 | <0.05 | <0.05 | <0.05 | <0.05 | | | | | ≤0.10% |
| Total Impurities | 0.8 | 0.8 | 0.7 | 1.1 | 0.7 | 0.7 | | | | | ≤2.0% |
| Loss on drying | 0.1 | <0.05 | <0.05 | 0.1 | <0.05 | 0.1 | | | | | ≤0.5% |
| Total aerobic microbial count | <10 | | | | <10 | <10 | | | | | ≤$10^3$ cfu/g |
| Total yeasts and moulds count | <10 | | | | <10 | <10 | | | | | ≤$10^2$ cfu/g |
| *Escherichia coli* | A | | | | A | A | | | | | Absence/g |

From the previous Tables 8 and Table 9 it has been confirmed that, in the accelerated stability conditions and long-term stability in the climatic area II, the measured parameters of the mannitol powder contained in the heat-sealed envelope object of the present invention remained stable throughout the duration of the test.

Innovatively, the present invention allowed to achieve the pre-set objectives.

More precisely, the process described above allows to effectively break-up the mannitol powder, generating favourable conditions for the subsequent filling of the containers.

Advantageously, the present invention allows to easily obtain a complete dissolution of mannitol in the working conditions of a final user.

Advantageously, the characteristics of the closure element and of the container were specially designed not only so as to ensure good dry storage, but also an easy opening of the container by a user.

Advantageously, the pH values explained above allow to accelerate the dissolution rate of mannitol, and thus to make the use of the present composition easier.

Advantageously, the design of the dissolving container allows to save a large amount of space, and/or weight, hence leading to a significant logistic and productive advantage.

Advantageously, the process subject of the present invention allows to compensate for the poor flowability of mannitol powder, which is assisted by the solvent when it comes to transfer.

Advantageously, the heat-sealed pouch containing the mannitol object of the present invention does not present any difficulty in disposal as a special waste, since mannitol is a natural product that does not require particular recovery attention, and the heat-sealed pouch can be disposed of in normal urban organic waste.

With respect to the embodiments of the aforementioned method, a man skilled in the art may replace or modify the described characteristics according to the contingencies. These variants are also to be considered included in the scope of protection as outlined in the claims that follow.

Furthermore, it should be observed that any embodiment may be implemented independently from the other embodiments described.

Further embodiments (FRn) of the present invention are reported below and claimed:

FR1. A container (1), preferably a single-dose container or a single-dose heat-sealed pouch, containing a single-dose composition of mannitol in powder form; said container (1) being obtainable or obtained by a process which comprises the following steps:
  a) breaking up a coherent mass of mannitol powder, so as to obtain a broken-up mass from said coherent mass;
  c) filling a plurality of containers with the broken-up mass of step a);
wherein the step a) comprises a breaking up carried out with a centrifugal force, and wherein a bulk density of the coherent mass is smaller than the bulk density of the broken-up mass.

FR2. The container (1) according to FR1, wherein a bulk density of the coherent mass is smaller than a bulk density of the broken-up mass by a percentage comprised from 1% to 40%, preferably comprised from 1% to 30%, even more preferably comprised from 5% to 15%, with respect to the bulk density of the broken-up mass.

FR3. The container (1) according to FR1 or FR2, wherein said centrifugal force is exerted through a centrifugal drum sieve.

FR4. The container (1) according to any of FR1-FR3, wherein step a) comprises the following sub-steps:
  a.i) sieving the coherent mass of mannitol powder; and
  a.ii) packing the product of sub-step a.i).

FR5. The container (1) according to any of FR1-FR4, wherein—in sub-step a.ii)—the mannitol powder is forced through a mesh with a clear gap comprised from 2.0 to 5.0 millimetres, preferably comprised from 2.0 to 4.0 millimetres, more preferably comprised from 2.5 to 3.5 millimetres, even more preferably of 3.0 millimetres.

FR6. The container (1) according to any of FR1-FR5, wherein a bulk density of mannitol powder at the end of sub-step a.ii) is comprised from 0.66 to 0.90 g/ml, preferably comprised from 0.66 to 0.84 g/ml, more preferably comprised from 0.68 to 0.78 g/ml, even more preferably comprised from 0.70 to 0.75 g/ml.

FR7. The container (1) according to any of FR1-FR6, wherein, at the end of step c), the mannitol powder in the container has a bulk density comprised from 0.40 to 0.65 g/ml.

FR8. The container (1) according to any of FR1-FR7, wherein, at the end of step c), the mannitol powder comprises an amount comprised from 90% to 100% by weight of powder particles with an average particle size comprised from 1 μm to 500 μm, preferably comprised from 1 μm to 400 μm, more preferably comprised from 1 μm to 300 μm.

FR9. The container (1) according to any of FR1-FR8, wherein the single-dose composition is devoid of excipients and/or pyrogenic substances.

FR10. The container (1) according to any of FR1-FR9, wherein the container (1) delimits a container compartment (4), wherein the container compartment (4) comprises a first volume fraction and a second volume fraction, and wherein—at the end of step c)—the first volume fraction is occupied by the single-dose composition, and the second volume fraction of said compartment is free from said composition, and preferably wherein the first volume fraction is about two-thirds of a total internal volume of the container compartment (4), the second volume fraction being about one-third of the total internal volume.

FR11. The container (1) according to any of FR1-FR10, wherein said single-dose composition comprises or consists of mannitol at an amount comprised from 50 to 200 grams, wherein said mannitol is in powder form, wherein said powder has a bulk density comprised from 0.40 to 0.65 g/ml and it comprises powder particles, wherein a percentage comprised from 90% to 100% by weight of the powder particles has an average particle size comprised from 1 μm to 500 μm.

FR12. The container (1) according to any of FR1-FR11, wherein the mannitol has a percentage by weight comprised from 97% to 100%, preferably a percentage by weight of 100%, with respect to the overall weight of said composition, wherein said bulk density of said powder is comprised from 0.50 g/ml to 0.62 g/ml, and wherein the single-dose composition is devoid of excipients and/or pyrogenic substances.

FR13. The container (1) according to any of FR1-FR12, wherein the single-dose composition which is present into said container (1), is for the use in the treatment of constipation, or for use as a purgative to be administered to a patient before performing an endoscopic examination.

FR14. The container (1), preferably a single-dose container or a single-dose heat-sealed pouch, in which said single-dose composition according to any of FR1-FR13, is contained in a container compartment (4) closed tightly by a closing element (6) removable.

FR15. The container (1) according to any one of FR1-FR14, wherein said container is a heat-sealed envelope, preferably a single-dose heat-sealed envelope, containing a single-dose composition according to any of the FR1-FR14, in a container compartment (4) seal-closed by a removable or tear-off closure element, in which said heat-sealed pouch is made of a polymeric material compostable according to the UNI EN 13432 or ASTM D6400 standard.

FR16. The container (1), according to any one of the FR1-FR15, in which the container compartment (4) comprises a first volume fraction and a second volume fraction, wherein the first volume fraction is occupied by the single-dose composition, of preference for about two thirds of a total internal volume of said compartment (4), and wherein the second volume fraction is free from said composition, preferably for about one third of the total internal volume.

FR17. Use of the single-dose composition of powdered mannitol contained in said container (1), according to any one of the FR1-FR16, in the treatment of constipation, or for use as a purgative to be administered to a patient before performing an endoscopic examination.

| LIST OF REFERENCE NUMBERS | |
|---|---|
| 1 | container, preferably single-dose |
| 2 | first lateral wall |
| 4 | containment compartment |
| 6 | closure element |
| 8 | first bottom wall |
| 10 | kit |
| 12 | first axial end |
| 14 | second axial end |
| 16 | access opening |
| 18 | first volume fraction |
| 20 | second volume fraction |
| 22 | vacant surface |
| 24 | funnel |
| 26 | inner compartment |
| 28 | level indicator |
| 30 | dissolving container |
| 32 | tamper-proof seal |
| 34 | second lateral wall |
| 36 | window or portion permeable to light |
| 38 | second bottom wall |
| 40 | first axial end |
| 42 | second axial end |
| 44 | access opening |
| 46 | coupling seat or housing seat |
| 48 | recess |
| 50 | bellows-like portion |
| 52 | outer tubular or annular portions |
| 54 | inner tubular or annular portions |
| 56 | material films |
| 58 | material films |
| 60 | peripheral portions |
| 62 | self-supporting bottom |
| 64 | powder-loading portion |
| 66 | powder-discharge portion |
| 68 | cap or closure member |
| 70 | container neck |
| 72 | complementary threaded means |
| 74 | filling device |
| 76 | coherent mass container |
| 78 | first conveying duct |
| 80 | drum centrifugal sieve shaker |
| 82 | suctioning means |
| 84 | second conveying duct |
| 86 | sieve shaker casing |
| 88 | mesh |
| 90 | sieve shaker drum |
| 92 | cylindrical compartment |
| 94 | radial openings |
| 96 | compressed air source |
| 98 | air duct |
| 100 | discharge opening |
| 102 | interspace |
| 104 | drum blade |
| R | rotation axis |
| S1 | displacement direction |
| S2 | displacement direction |
| S3 | discharge direction |
| X | first main extension axis |
| Y | second main extension axis |

The invention claimed is:

1. A method for filling containers with a composition that comprises or, alternatively, consists of mannitol in powder form, comprising:
 a) breaking up a coherent mass of mannitol powder using a centrifugal drum sieve having a mesh gap size in the range of 2.0-5.0 millimeters, so as to obtain a broken-up mass from said coherent mass; and
 b) filling a plurality of containers with the broken-up mass of step a)
 wherein each container comprises a container compartment that comprises a first volume fraction and a second volume fraction, wherein at the end of step b) the first volume fraction is occupied by a single-dose composition and the second volume fraction is free from said composition, and wherein the first volume fraction is about two-thirds of a total internal volume of the container compartment and the second volume fraction is about one-third of the total internal volume.

2. The method according to claim 1, wherein a bulk density of the coherent mass is smaller than a bulk density of the broken-up mass by a percentage in the range of 1% to 40%, with respect to the bulk density of the broken-up mass.

3. The method according to claim 2, wherein the bulk density of the coherent mass is smaller than the bulk density of the broken-up mass by a percentage in the range of 1% to 30%.

4. The method according to claim 3, wherein the bulk density of the coherent mass is smaller than the bulk density of the broken-up mass by a percentage in the range of 5% to 15%.

5. The method according to claim 1, wherein step a) comprises the following sub- steps:
   a. i) sieving the coherent mass of mannitol powder; and
   a. ii) packing the product of sub-step a.i).

6. The method according to claim 5, wherein- in sub-step a.ii)- the mannitol powder is forced through a mesh with a clear gap in the range of 2.0 to 4.0 millimetres.

7. The method according to claim 5, wherein a bulk density of mannitol powder at the end of sub-step a.ii) is in the range of 0.66 to 0.90 g/ml.

8. The method according to claim 7, wherein the bulk density of mannitol powder at the end of sub-step a.ii) is in the range of 0.66 to 0.84 g/ml.

9. The method according to claim 8, wherein the bulk density of mannitol powder at the end of sub-step a.ii) is in the range of 0.68 to 0.78 g/ml.

10. The method according to claim 9, wherein the bulk density of mannitol powder at the end of sub-step a.ii) is in the range of 0.70 to 0.75 g/ml.

11. The method according to claim 1, wherein, at the end of step b), the mannitol powder in the container has a bulk density in the range of 0.40 to 0.65 g/ml.

12. The method according to claim 1, wherein, at the end of step b), the mannitol powder comprises an amount in the range of 90% to 100% by weight of powder particles with an average particle size in the range of 1 μm to 500 p.m.

13. The method according to claim 12, wherein, the average particle size is in the range of 1 μm to 400 μm.

14. The method according to claim 13, wherein, the average particle size is in the range of 1 μm to 300 μm.

15. The method according to claim 1, wherein the single-dose composition is devoid of excipients and/or pyrogenic substances.

16. The method according to claim 1, wherein the centrifugal drum sieve further comprises an air compressor and the powdered mannitol is pushed through the centrifugal drum sieve by compressed air in step (a).

* * * * *